United States Patent
Tachibana et al.

[11] Patent Number: 6,001,069
[45] Date of Patent: Dec. 14, 1999

[54] ULTRASOUND CATHETER FOR PROVIDING A THERAPEUTIC EFFECT TO A VESSEL OF A BODY

[75] Inventors: Katsuro Tachibana, Fukuoka, Japan; Douglas R. Hansmann, Bainbridge Island; James R. Anderson, Redmond, both of Wash.

[73] Assignee: Ekos Corporation, Bothell, Wash.

[21] Appl. No.: 09/071,285

[22] Filed: May 1, 1998

Related U.S. Application Data

[60] Provisional application No. 60/045,268, May 1, 1997.

[51] Int. Cl.⁶ .................................................. A61H 1/00
[52] U.S. Cl. ................................................ 601/2; 604/22
[58] Field of Search ...................... 600/437, 438, 600/459, 462, 466, 467, 471, 439; 604/22; 601/2; 606/1, 159, 169

[56] References Cited

U.S. PATENT DOCUMENTS

| | | | |
|---|---|---|---|
| 3,433,226 | 3/1969 | Boyd | 128/305 |
| 4,040,414 | 8/1977 | Suroff | 128/24 |
| 4,319,580 | 3/1982 | Colley et al. | 128/661 |
| 4,354,502 | 10/1982 | Colley et al. | 128/663 |
| 4,531,943 | 7/1985 | Van Tassel et al. | 604/280 |
| 4,549,533 | 10/1985 | Cain et al. | 128/24 |
| 4,750,902 | 6/1988 | Wuchinich et al. | 604/22 |
| 4,808,153 | 2/1989 | Parisi | 604/22 |
| 4,870,953 | 10/1989 | Don Micheal et al. | 128/24 |
| 4,920,954 | 5/1990 | Alliger et al. | 128/24 |
| 4,924,863 | 5/1990 | Sterzer | 606/27 |
| 4,936,281 | 6/1990 | Stasz | 128/660.03 |
| 5,021,044 | 6/1991 | Shakawy | 604/53 |
| 5,163,421 | 11/1992 | Bernstein et al. | 128/24.1 |
| 5,197,946 | 3/1993 | Tachibana | 604/22 |
| 5,207,214 | 5/1993 | Romano | 128/24 |
| 5,250,034 | 10/1993 | Appling et al. | 604/164 |
| 5,267,954 | 12/1993 | Nita | 604/22 |
| 5,267,985 | 12/1993 | Shimada et al. | 604/290 |
| 5,269,291 | 12/1993 | Carter | 128/24 |
| 5,282,785 | 2/1994 | Shapland et al. | 604/21 |
| 5,286,254 | 2/1994 | Shapland et al. | 604/21 |
| 5,295,484 | 3/1994 | Marcus et al. | 600/439 |
| 5,304,115 | 4/1994 | Pflueger et al. | 604/22 |
| 5,307,816 | 5/1994 | Hashimoto et al. | 601/2 |
| 5,318,014 | 6/1994 | Carter | 601/2 |
| 5,323,769 | 6/1994 | Bommannan et al. | 601/2 |
| 5,327,891 | 7/1994 | Rammler | 128/658 |
| 5,328,470 | 7/1994 | Nabel et al. | 604/101 |
| 5,344,435 | 9/1994 | Turner et al. | 607/101 |
| 5,345,940 | 9/1994 | Seward et al. | 128/662.06 |
| 5,353,798 | 10/1994 | Sieben | 128/662.06 |
| 5,354,279 | 10/1994 | Hofling | 604/164 |
| 5,362,309 | 11/1994 | Carter | 604/22 |
| 5,363,853 | 11/1994 | Lieber | 128/662.06 |
| 5,380,273 | 1/1995 | Dubrul et al. | 604/22 |
| 5,385,148 | 1/1995 | Lesh et al. | 600/462 |
| 5,390,678 | 2/1995 | Gesswein et al. | 128/662.06 |
| 5,421,338 | 6/1995 | Crowley et al. | 128/662.06 |
| 5,423,797 | 6/1995 | Sorin et al. | |
| 5,431,663 | 7/1995 | Carter | 604/128 |
| 5,445,155 | 8/1995 | Sieben | 128/660.07 |

(List continued on next page.)

FOREIGN PATENT DOCUMENTS

| | | | |
|---|---|---|---|
| 0 529 675 | 8/1992 | European Pat. Off. | A61B 17/06 |
| 0 629 382 | 11/1993 | European Pat. Off. | A61B 17/36 |
| 40 05 743 | 8/1991 | Germany | A61H 23/00 |
| 4005743 A1 | 8/1991 | Germany . | |
| WO 89/04142 | 5/1989 | WIPO | A61B 8/12 |
| WO 95/01751 | 1/1995 | WIPO | A61B 8/12 |
| WO 96/29935 | 10/1996 | WIPO | A61B 8/12 |
| WO 98/11826 | 3/1998 | WIPO | A61B 17/00 |
| WO 98/48711 | 11/1998 | WIPO | A61B 17/22 |

*Primary Examiner*—Francis J. Jaworski
*Assistant Examiner*—Ali M. Imam
*Attorney, Agent, or Firm*—Wilson, Sonsini, Goodrich & Rosati; Travis L. Dodd

[57] ABSTRACT

A catheter for use in a vessel of a body is disclosed. The catheter includes an elongated body and a plurality of ultrasound elements coupled to the elongated body. Each of the plurality of ultrasound elements is separated from an adjacent ultrasound element.

22 Claims, 6 Drawing Sheets

U.S. PATENT DOCUMENTS

| | | | |
|---|---|---|---|
| 5,447,509 | 9/1995 | Mills et al. | 606/1 |
| 5,458,568 | 10/1995 | Racchini et al. | 604/19 |
| 5,465,726 | 11/1995 | Dickinson et al. | 128/663.01 |
| 5,474,530 | 12/1995 | Passafaro et al. | 604/22 |
| 5,474,531 | 12/1995 | Carter | 604/22 |
| 5,498,238 | 3/1996 | Shapland et al. | 604/53 |
| 5,509,896 | 4/1996 | Carter | 604/21 |
| 5,514,092 | 5/1996 | Forman et al. | 604/101 |
| 5,520,189 | 5/1996 | Malinowski et al. | 128/662.03 |
| 5,603,327 | 2/1997 | Eberle | 128/662.06 |
| 5,606,974 | 3/1997 | Castellano et al. | 600/438 |
| 5,617,851 | 4/1997 | Lipkovker | 128/632 |
| 5,618,275 | 4/1997 | Bock | 604/290 |
| 5,620,479 | 4/1997 | Diederich | 607/97 |
| 5,628,730 | 5/1997 | Shapland | 604/21 |
| 5,725,494 | 3/1998 | Brisken | 604/22 |

ULTRASOUND CATHETER FOR PROVIDING A THERAPEUTIC EFFECT TO A VESSEL OF A BODY

RELATIONSHIP TO COPENDING APPLICATIONS

This application is a continuation-in-part of Provisional U.S. patent application Ser. No. 60/045,268; Filed: May 1, 1997 entitled Side Delivery Catheter.

BACKGROUND OF THE INVENTION

1. Field of the Invention

The present invention relates to an ultrasound enhanced drug delivery catheter, and more particularly, to an ultrasound enhanced drug delivery catheter with a plurality of ultrasound elements.

2. Description of Related Art

Thrombus formation is a protective and healing mechanism, however, formation of thrombi can be detrimental. For instance, if a blood vessel becomes blocked, distal tissue may be deprived of oxygen with resulting damage or necrosis. In the case of cerebral circulation, an arterial thrombus blockage is one cause of cerebral strokes. In the case of coronary thrombosis, blockage and subsequent distal tissue necrosis of cardiac muscle tissue will impair cardiac pump output, may cause electrical abnormalities, and potentially catastrophic heart failure and death. The thrombus can form at the site of artery narrowing due to arterial wall damage or disease, or the thrombus may have broken free from some proximal site only to become wedged in a distal stenosis. Thrombus can also form subsequent to attempts to remove a stenosis using balloon angioplasty or rotary atherectomy.

Ultrasound catheters have been described specifically for removal or dissolution of thrombus (U.S. Patents: Tachibana U.S. Pat. No. 5,197,946; Bernstein U.S. Pat. No. 5,163,421; Weng U.S. Pat. No. 5,269,297). The catheters of Bernstein and Weng place an ultrasound generator external to the body and transmit acoustic energy through a metal wire waveguide to the distal catheter. The catheter of Tachibana includes a small ultrasound element positioned at the distal end of the catheter that is energized by electrical wires. In either case, ultrasound energy is delivered to and radiated from the distal tip of the catheter in the vicinity of a blocking thrombus. The application of ultrasound can directly emulsify nearby thrombus through the motion of the catheter tip and associated cavitation.

The application of ultrasound can also enhance delivery of drug into a vessel wall. There are instances where the vessel wall is diseased or has been injured such as balloon angioplasty or rotary atherectomy. Narrowing of the vessel can occur in response to these injuries. Certain drugs, such as heparin, may inhibit this narrowing of the blood vessel if the drug can be delivered into the blood vessel wall. A catheter can be used to deliver drugs into any portion of the body or target organ. Ultrasound energy in the presence of these drugs can enhance the delivery through and across bodily fluids and tissue. Hence, an ultrasound drug delivery catheter placed in a blood vessel will assist delivery across the blood vessel wall, whether it be an artery or a vein, into the surrounding muscle or tissue.

The intensity of the ultrasound delivered from an ultrasound element decreases exponentially with radial distance from the catheter tip. Hence, treatment of thrombi is limited to a few millimeters of the catheter tip of a catheter with an ultrasound element. This small treatment area may be effective for small volume clots, however, larger clots must be treated one section at a time.

Some thrombi can be large. For instance, a deep vein thrombus in a patient's lower leg and can have a length from several centimeters to as much as 12 to 20 inches long. Early treatment protocols for these long thrombi used a drug infusion catheter to drip lytic drug at one end of a thrombus. As the thrombus was dissolved, the catheter would be advanced. This process was repeated until the entire clot was dissolved. More current therapy for a deep vein thrombosis is to use an infusion catheter with drug infusion ports distributed along the lateral dimension of the catheter. The catheter can be pushed through the entire length of the clot. The thrombolytic drug is then infused throughout the lesion for a period of hours.

There is a need for an ultrasound catheter that is useful for treating a deep vein thrombus to enhance and accelerate the action of the thrombolytic drug. There is a further need for an ultrasound catheter that is useful for treating vessel lesions, particularly those that have extensive lengths.

SUMMARY OF THE INVENTION

An object of the invention is to provide a catheter with an ultrasound element.

A further object of the invention is to provide a catheter with segmented ultrasound elements.

Another object of the invention is to distribute the ultrasound radiation along a portion of the length of the catheter.

Another object of the invention is to increase the flexibility of a catheter with large ultrasound emitter surface areas.

A further object of the invention is to reduce the cross sectional area of the wiring associated with large ultrasound emitter surface areas.

Yet another object of the invention is to provide a catheter with segmented ultrasound emitters which require less power than a single, long, ultrasound emitter.

The above objects can be achieved with a catheter for use in a vessel of a body. The catheter includes an elongated body and a plurality of ultrasound elements coupled to the elongated body. Each of the plurality of ultrasound elements is separated from an adjacent ultrasound element.

Another embodiment of the catheter includes a flexibility providing structure positioned between two ultrasound elements among the plurality of ultrasound elements. The flexibility providing structure can be a rib, a braided material and a mesh material.

DETAILED DESCRIPTION

Figure 1A:
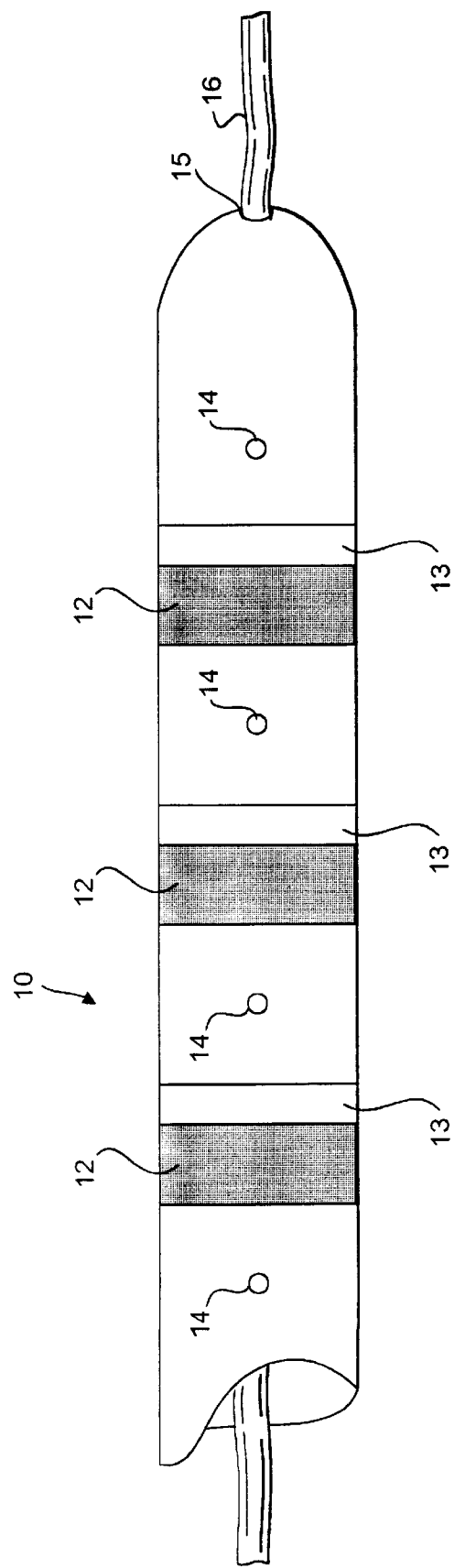
FIG. 1A is a sideview of a catheter with segmented ultrasound elements.

FIG. 1A illustrates an ultrasound catheter 10 which includes a plurality of ultrasound elements 12, temperature sensors 13 and drug delivery ports 14 positioned along a selected section of the catheter 10. The catheter 10 also includes a guidewire lumen 15 which can accommodate a guidewire 16. At least one drug delivery port 14 is correlated with each ultrasound element 12.

Figure 1B:
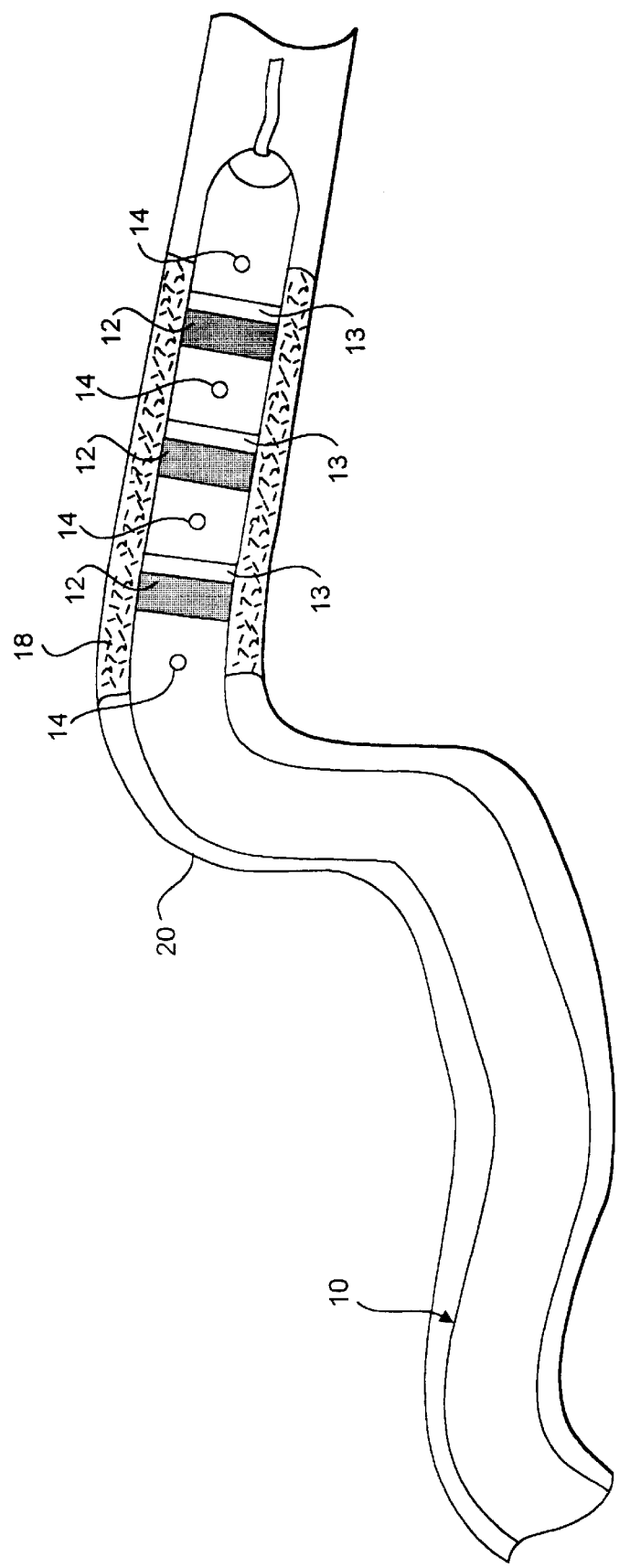
FIG. 1B illustrates the catheter of FIG. 1A positioned within a vessel of a body.

In operation, the ultrasound elements 12 and drug delivery ports 14 can be positioned adjacent a large lesion 18 in a vessel 20 as illustrated in FIG. 1B. Discrete ultrasound elements 12 are used in comparison to one continuous ultrasound element. Catheters introduced through circulatory vessels must be flexible in order to reach a desired location where the lesion 18 is located. When a large lesion 18 is present, a single ultrasound element which is long enough to deliver ultrasound energy the length of the lesion reduces the flexibility of the catheter 10. Therefore, multiple segmented ultrasound elements 12 provide an increased flexibility over a long single element.

The average power required to activate an ultrasound element 12 is proportional to the activated area of the ultrasound element 12. Hence, a 2-cm long element requires approximately twice as much power as a 1-cm long element of similar shape and diameter. As the power increases, the diameter of the electrical wires that bring electrical energy to the ultrasound elements 12 must also increase. This requires an increase in catheter diameter that in turn reduces flexibility and restricts use of the catheter 10 in larger vessels.

These difficulties are solved by the present invention that creates a distribution of smaller ultrasound elements 12. The ultrasound elements 12 are sized small enough so that they in combination with the catheter 10 provide a flexible structure that can be moved down a tortuous vein tree to the site of the lesion 18 or to any vessel in which there is a lengthy lesion 18 to be treated. Additionally, the ultrasound elements 12 are small enough that each individual ultrasound element 12, if excited individually, does not take an inordinate amount of power through the wires which supply power to the catheter 10. The ultrasound elements 12 are positioned to reduce dead space between the ultrasound elements 12. This provides some overlap in the radiation patterns that emit from each of the ultrasound elements 12 to maximize the enhancement effect. There is also a proximity between the ultrasound element 12 and the drug delivery ports 14 so that the drug emitted proximal or next to the catheter 10 is then affected by a nearby source of ultrasound energy. However, the drug delivery ports 14 do not need to be correlated with a particular ultrasound element 12 and there need be no relationship between the number of drug delivery ports 14 and the number of ultrasound elements 12.

The ultrasound energy can be generated at an ultrasound energy source located external to the body and transmitted via wire to the ultrasound elements. Ultrasound can also be internally generated from electrical power delivered to the ultrasound elements from an electrical energy source. A suitable example of an ultrasound element for internal generation of ultrasound energy includes, but is not limited to, a piezoelectric ceramic oscillators. The ultrasound elements can be shaped as a cylinder, a hollow cylinder and a disk which are concentric with the catheter. The ultrasound elements can also be an array of smaller ultrasound elements or a thin plate positioned within the body of the catheter. Similarly, a single ultrasound element can be composed of several smaller ultrasound elements.

Figure 2A:
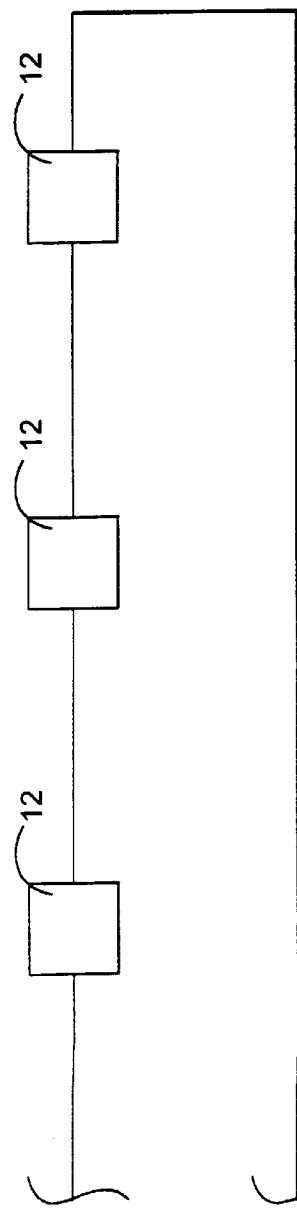
FIG. 2A illustrates ultrasound elements connected in series.
Figure 2B:
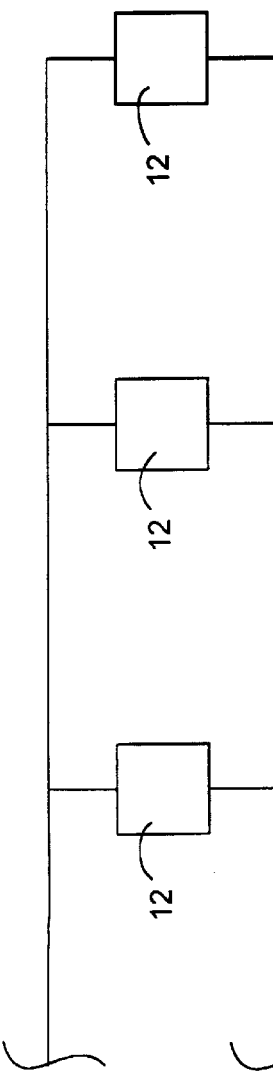
FIG. 2B illustrates ultrasound elements connected in-parallel.

The individual ultrasound elements 12 can each be individually powered. When the catheter includes N ultrasound elements, the catheter body must include 2N wires to individually power N ultrasound elements 12. The individual ultrasound elements 12 can also be electrically coupled in serial or in parallel as illustrated in FIGS. 2A and 2B. These arrangements permit maximum flexibility as they require only 2N wires. Each of the ultrasound elements receives power simultaneously whether the ultrasound elements are in series or in parallel. When the ultrasound elements 12 are in series, less current is required to produce the same power from each ultrasound element 12 than when the ultrasound elements 12 are connected in parallel. The reduced current allows smaller wires to be used to provide power to the ultrasound elements 12 and accordingly increases the flexibility of the catheter 10. When the ultrasound elements 12 are connected in parallel, an ultrasound element 12 can break down and the remaining ultrasound elements 12 will continue to operate.

Figure 2C:
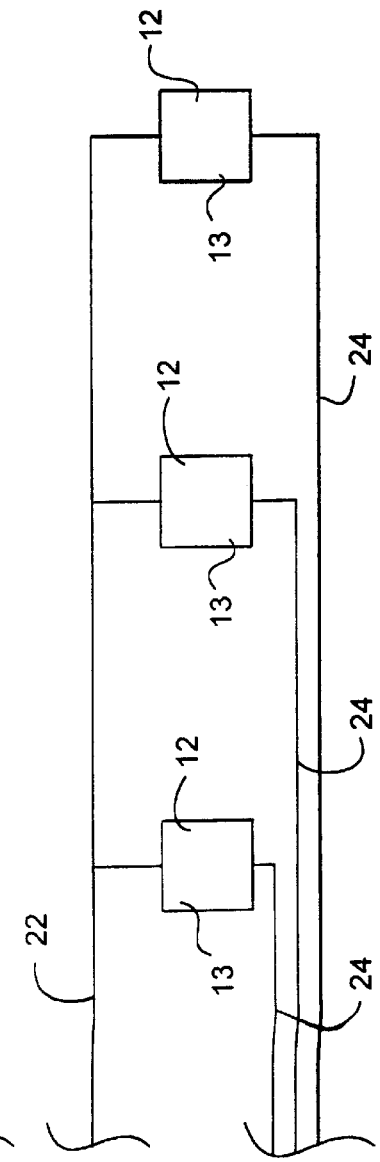
FIG. 2C illustrates ultrasound elements or temperature sensors connected through a common wire.

As illustrated in FIG. 2C, a common wire 22 can provide power to each of the ultrasound elements 12 while each ultrasound element 12 has its own return wire 24. A particular ultrasound elements 12 can be individually activated by closing a switch (not shown) to complete a circuit between the common wire 22 and the particular ultrasound element's return wire 24. Accordingly, a catheter with N ultrasound elements requires only N+1 wires and still permits independent control of the ultrasound elements 12. This reduced number of wires increases the flexibility of the catheter 10. To improve the flexibility of the catheter, the individual return wires can have diameters which are smaller than the common wire diameter. For instance, in an embodiment where N ultrasound elements will be powered simultaneously, the diameter of the individual wires can be the square root of N times smaller than the diameter of the common wire.

As illustrated in FIG. 1, a temperature sensor 13 is positioned adjacent each ultrasound element 12. Suitable temperature sensors 13 include, but are not limited to, thermistors, thermocouples and resistance temperature detectors, RTDs, and fiber optic temperature sensors which use thermalchromic liquid crystals. Suitable temperature sensor 13 geometries include, but are not limited to, a point, patch, stripe and a band around the catheter 10 as illustrated. The temperature sensors 13 can be positioned on the catheter 10, on the ultrasound element and adjacent the ultrasound elements 12 as illustrated.

The temperature sensors 13 can be electrically connected as illustrated in FIG. 2C. Each temperature sensor 13 can be coupled with a common wire 22 and then include its own return wire 24. Accordingly, N+1 wires can be used to independently sense the temperature at the temperature sensors 13 of a catheter 10 having N temperature sensors 13. A suitable common wire 22 can be constructed from Constantine and suitable return 24 wires can be constructed from copper. The temperature at a particular temperature sensor 13 can be determined by closing a switch (not shown) to complete a circuit between the thermocouple's return wire 24 and the common wire 22. When the temperature sensors 13 are thermocouples, the temperature can be calculated form the voltage in the circuit. To improve the flexibility of the catheter, the individual return wires can have diameters which are smaller than the common wire diameter.

Each temperature sensor 13 can also be independently wired. A catheter 10 including N temperature sensors 13 which are independently wired will require 2N wires to pass the length of the catheter.

The catheter flexibility can also be improved by using fiber optic based temperature sensors. The flexibility can be improved because only N fiber optics need to be included in the catheter to sense the temperature at N temperature sensors.

The temperature sensors 13 do not need to be correlated with the ultrasound elements 12. For instance, the catheter 10 can include a temperature sensor 13 which is positioned to provide a signal indicating the temperature of the portion of the lumen being treated. For instance, the temperature sensor 13 can be positioned between the central two ultrasound elements. The ultrasound output from the ultrasound elements 12 can be manually or automatically adjusted in response to the signal from the temperature sensor 13.

Figure 3A:
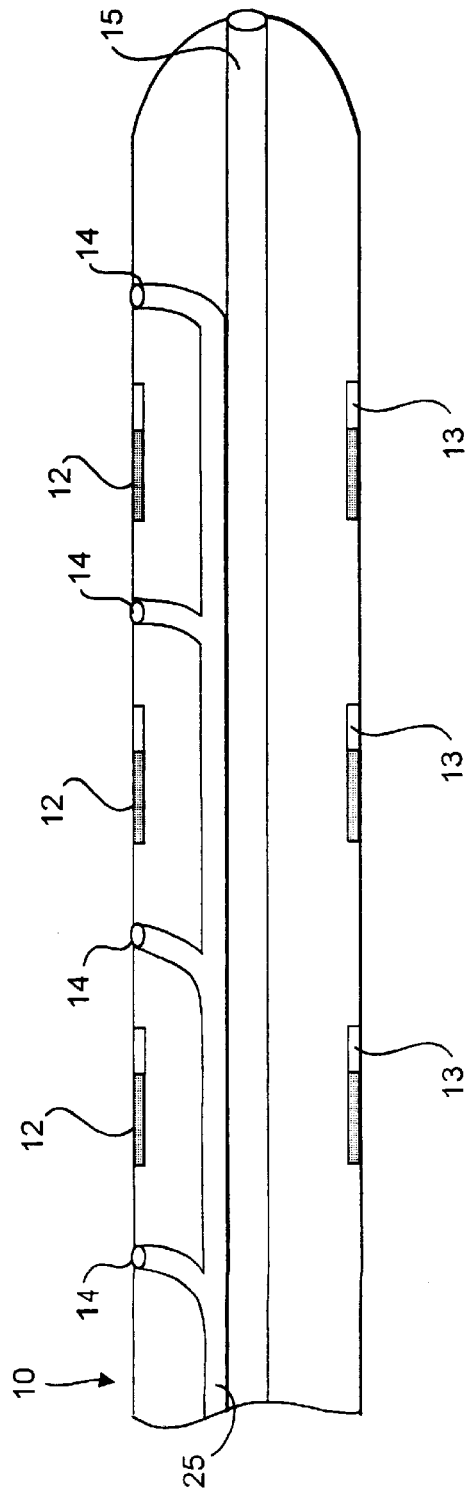
FIG. 3A is a cross section of a catheter with a lumen coupled with drug delivery ports which are each correlated with an ultrasound element.
Figure 3B:
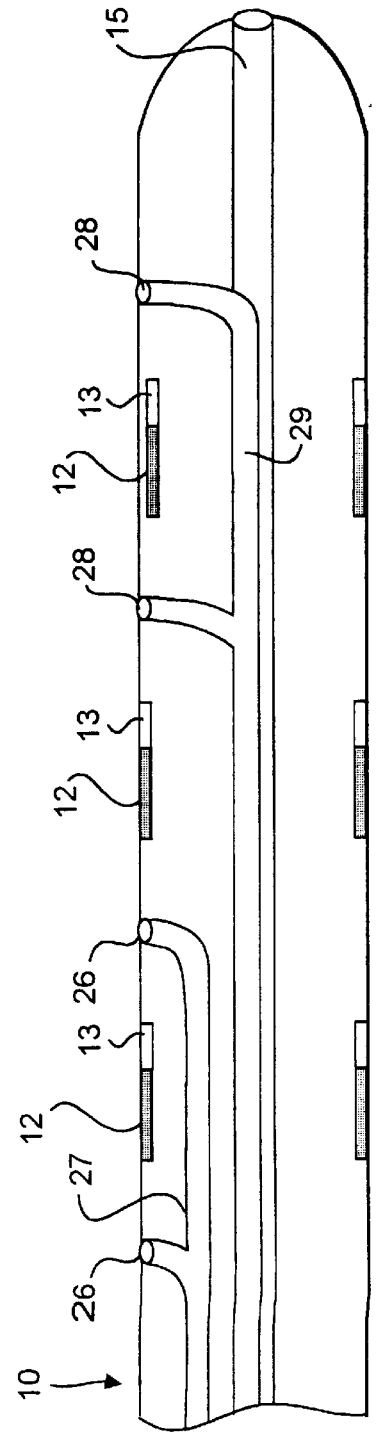
FIG. 3B is a cross section of a catheter with a first lumen for delivering drug through first drug delivery ports and a second lumen for delivering drug through second drug delivery ports.

The drug delivery ports 14 can be coupled with a common lumen 25 as illustrated in FIG. 3A. The drug delivery ports 14 can be positioned on one side of the catheter 10 or distributed about the surface of the catheter 10 to provide a more even delivery of the drug. A drug can be delivered through the common lumen 25 to the various drug delivery ports 14 next to each of the ultrasound elements 12 so that all of the drug delivery ports 14 deliver drug at the same time. As illustrated in FIG. 3B, one or more drug delivery ports 26 can be coupled with a first lumen 27 and one or more second drug delivery ports 28 can be coupled with a second lumen 29. Accordingly, different drugs can be delivered adjacent different ultrasound elements 12. Further, different amounts of the same drug can be delivered adjacent particular ultrasound elements 12. As a result, the amount of drug delivery can be adjusted to match the amount of therapeutic treatment required by a particular section of the lesion 18. Use of the ultrasound elements 12 and a plurality of drug delivery ports 14 can provide controllability and selectability of lesion modification/destruction.

The catheter 10 can be used in various body structures and body lumens including, but not limited to, the pancreas, sinuses, esophagus, rectum, gastrointestinal vessels and urological vessels. The catheter 10 is selected from a variety of different sizes, diameter and length, depending on the type and location of the lesion 18. An active length of catheter 10 is defined by the number and spacing of the ultrasound elements 12 and drug delivery ports 14 at the distal end. The number of ultrasound elements 12 depends on the length of the vessel being treated. Suitable numbers of ultrasound elements include, but are not limited to 2–10, 2–8 and 4–6. Each of the ultrasound elements 12 can be from one millimeter in length to up to a half centimeter in length. Other dimensions can also be used. The spacing between ultrasound elements 12 can be approximately equal to the length of each ultrasound element 12. If one ultrasound element 12 has a length L, a second ultrasound element 12 can be spaced up to three L lengths away from the first ultrasound element 12. Suitable L include, bur are not limited to 0.2–2 cm, 0.2–1.2 cm and 0.3–0.7 cm.

Figure 4A:
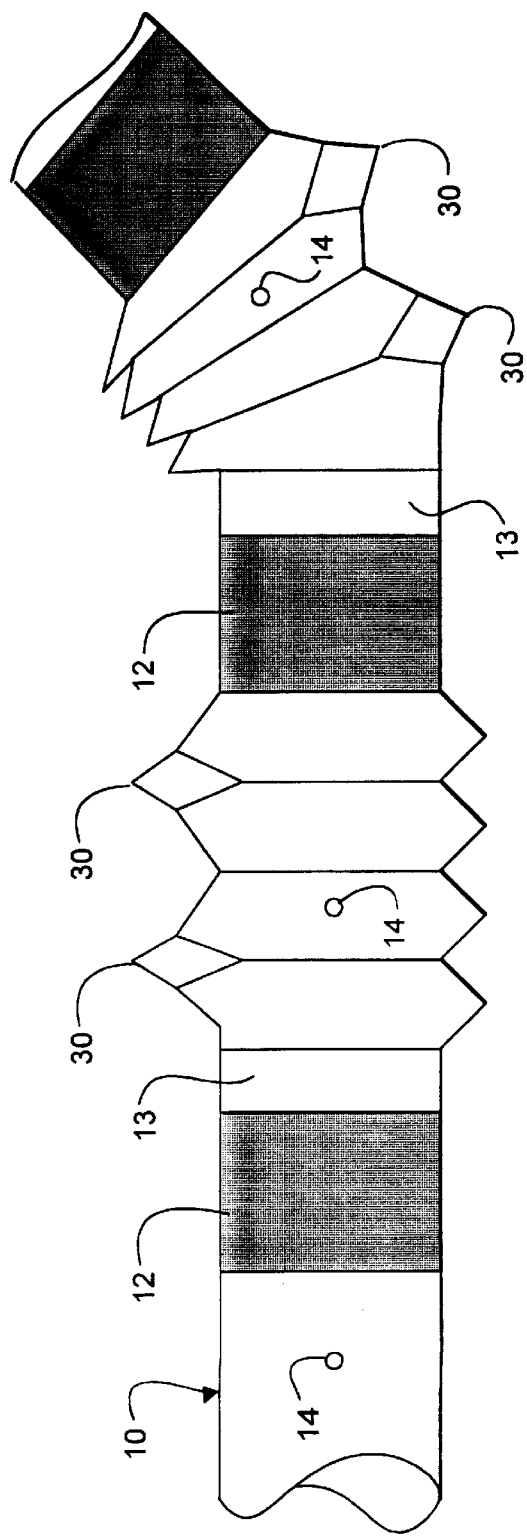
FIG. 4A is a sideview of a catheter including ribs between ultrasound elements.
Figure 4C:
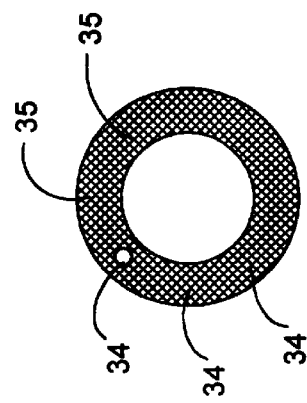
FIG. 4C is a cross section of the catheter of FIG. 4B.
Figure 4B:
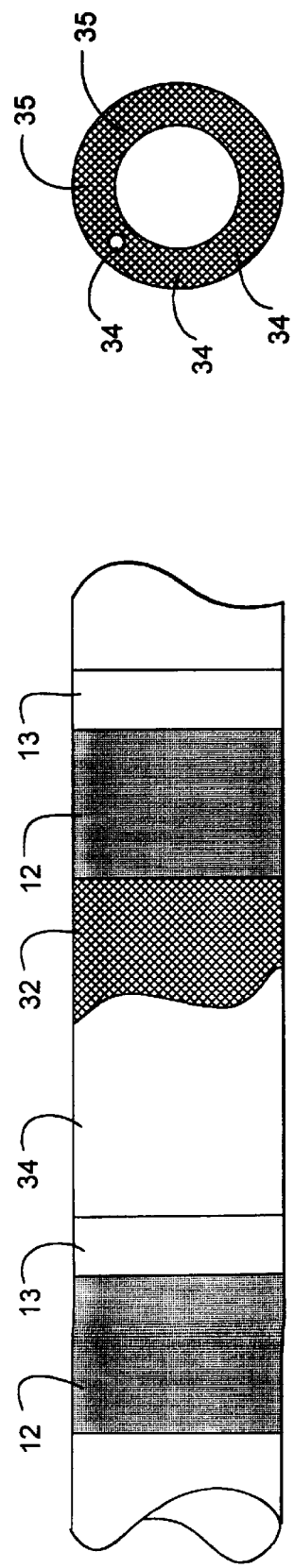
FIG. 4B is a cut-away view a catheter including webbing or mesh between the ultrasound elements.

The catheter 10 can be constructed to overcome the reduced flexibility which results from the multiple ultrasound elements 12. As illustrated in FIG. 4A, the catheter 10 can include ribs 30 between the ultrasound elements 12. The ribs 30 increase the bendability of the catheter at the ribbed locations while providing kink resistance. The added flexibility can be necessary to work the catheter 10 through tortuous vessels. As illustrated in FIG. 4B additional flexibility can be obtained by manufacturing at least the portion of the catheter 10 between the ultrasound elements 12 from a mesh 32 or braided material. As illustrated in FIG. 4C, the outer surface of the catheter 10 and the lumens within the catheter 10 are smooth 34. The smooth surfaces 34 aid in passing the catheter 10 through the body lumen and in passing fluids through the lumen. Any wires 35 present in the catheter 10 can pass through the mesh portion of the catheter 10 for additional flexibility. Suitable materials for the catheter include, but are not limited to polyolefins and polyimides and other low acoustic impedance materials. Low accoustic impedance materials are materials which readily transmit ultrasound energy with minimal absorption of the energy. Suitable materials for the mesh or braid include, but are not limited to Kevlar, stainless steel, polyetheretherketone or PEEK. Cotton braided with polymer can also serve to provide flexibility and kink resistance.

The ultrasound elements 12 can be positioned internally or externally to catheter 10, and can have any number of different geometric designs. Suitable, geometric designs include, but are not limited to a band which lies flush with the circumference of the catheter. Additionally, ultrasound elements 12 can be designed provide any desired directionality of ultrasound.

Figure 5:
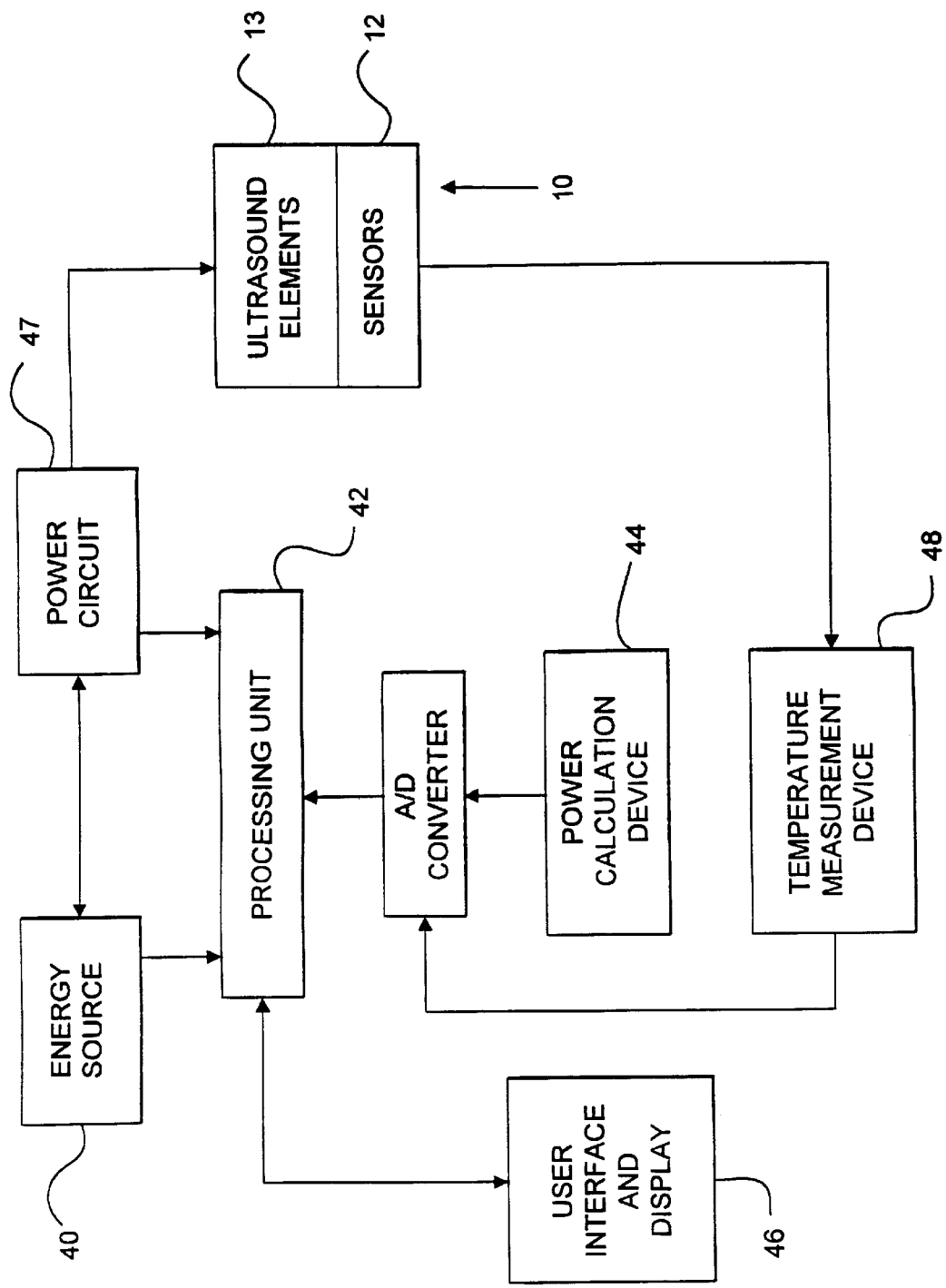
FIG. 5 is a schematic of a feedback control system for a catheter including a plurality of ultrasound elements.

The catheter 10 can be coupled with an open or closed loop feedback system. Referring now to FIG. 5 an open or closed loop feedback system couples temperature sensor 13 to an energy source 40. The temperature of the tissue, or of each ultrasound element 12 is monitored, and the output power of energy source 40 adjusted accordingly. The physician can, if desired, override the closed or open loop system. A processing unit 42 can be included and incorporated in the closed or open loop system to switch power on and off, as well as modulate the power. The processing unit 42 includes logic for monitoring the temperature at each temperature sensor 13, adjusting the power delivered to each ultrasound element 12, re-monitoring the temperature at each temperature sensor 13 and re-adjusting the power delivered to the ultrasound elements 12 in response to the re-monitored temperature.

With the use of the temperature sensors 13 and the feedback control system, the tissue adjacent to the ultrasound elements 12 can be maintained at a desired temperature for a selected period of time. Each ultrasound element 12 is connected to resources which generate an independent output. The output maintains a selected energy at each ultrasound element 12 for a selected length of time.

Power delivered to the ultrasound elements 12 is measured by the power calculation device 44. The power can then be displayed at user interface and display 46. Signals representative of power and impedance values are received by the processing unit 42.

A control signal is generated by the processing unit 42 that is proportional to the difference between an actual measured value, and a desired value. The control signal is used by power circuits 47 to adjust the power output in an appropriate amount in order to maintain the temperature at each ultrasound element 12 within a desired range.

The temperatures detected at the temperature sensors 13 provide feedback for maintaining the desired temperature range. The temperature at each temperature sensor 12 can be used as safety devices to interrupt the delivery of energy when maximum pre-set temperatures are exceeded. The temperature at each ultrasound sensor 12 is measured at temperature measurement device 48, and can be displayed at user interface and display 46. A temperature control signal is generated by the processing unit 42 that is proportional to the difference between an actual measured temperature and a desired temperature. The temperature control signal is used to determine the desired power. For instance, when the control signal exceeds a pre-determined level, the desired power supplied to a particular ultrasound element can be reduced or turned off. Similarly, when the control signal falls below a pre-determined level, the desired power supplied to a particular ultrasound element 12 can be increased or turned on.

The processing unit 42 can be a digital or analog controller, or a computer with software. When the processing unit 42 is a computer it can include a CPU coupled through a system bus. On this system can be a keyboard, a disk drive, or other non-volatile memory systems, a display, and other peripherals, as are known in the art. Also coupled to the bus is a program memory and a data memory.

User interface and display 46 includes operator controls and a display.

The output of the temperature sensors 13 is used by the processing unit 42 to maintain a selected temperature range at each temperature sensor 13. A profile of the power delivered to each ultrasound element 12 can be incorporated in the processing unit 42 and a preset amount of energy to be delivered may also be profiled.

Circuitry, software and feedback to the processing unit 42 result in process control, and the maintenance of the selected power setting that is independent of changes in voltage or current, and used to change, (i) the selected power setting, (ii) the duty cycle (on-off time), (iii) bipolar or monopolar energy delivery and (iv) fluid delivery, including flow rate and pressure. These process variables are controlled and varied, while maintaining the desired delivery of power independent of changes in voltage or current, based on temperatures monitored at the temperature sensor 13.

The catheter 10 is guided along the artery or vein to the lesion site by fluoroscopy. Radio opaque markers may be used with the catheter 10 next to each of the ultrasound elements 12, or in the case of certain piezoelectric elements 12, the ultrasound elements 12 themselves are radio opaque and readily identified and also readily identify the site of the adjacent drug port 14. The catheter 10 is advanced through the vessel with the assistance of a guidewire. The catheter can be advanced until each of the ultrasound elements are adjacent the lesion or until only a portion of the ultrasound elements are adjacent the lesion. The drug is hydraulically delivered through the lumen to the drug delivery ports 14. The ultrasound elements 12 are then all turned on together, sequenced or multiplexed according to the preferred treatment by the physician. The feedback control system is then engaged to control the temperature of within the vessel. The catheter 10 remains in place for the treatment period and the drug can be continually infused with the ultrasound elements 12 on, off, partially on, or partially off. After a section of the vessel is treated, the catheter can be advanced to treat additional untreated portions of the vessel. The ultrasound elements which are used to treat the additional untreated portion can be different from the ultrasound elements used during the initial treatment(s). When the desired clinical result is obtain, as verified by fluoroscopy, the catheter 10 is removed.

Segmentation of ultrasound elements 12 greatly reduces the required amount of a lumen of the catheter 10 that is used for segment wiring, increases the flexibility of the catheter 10, and permits radiation of a long lesion 18. When a single continuous length ultrasound element is used the power requirements necessitate the use of thick wires. This is eliminated with the use of ultrasound elements 12 in segment form. Replacement of one large wire by multiple wires of equivalent cross-sectional area or a cumulated cross-section area is more flexible and also avoids having to excite entirely a long ultrasound element, smaller ultrasound elements 12 that are segmented are used. Therefore, a fraction of the power at any one time is needed, depending on the number of ultrasound elements 12 activated.

The foregoing description of a preferred embodiment of the invention has been presented for purposes of illustration and description. It is not intended to be exhaustive or to limit the invention to the precise forms disclosed. Obviously, many modifications and variations will be apparent to practitioners skilled in this art.

What is claimed is:

1. A catheter for providing a therapeutic effect to a vessel of a body, comprising:

an elongated body having a lumen coupled with a drug delivery port through which a drug within the lumen can exit the lumen; and a plurality of ultrasound elements coupled to the elongated body where each of the plurality of ultrasound elements is separated from an adjacent ultrasound element and at least two of the ultrasound elements are positioned on opposite sides of the drug delivery port and close enough to the drug delivery port that a drug delivered from the drug delivery port is exposed to ultrasound energy delivered from at least one of the ultrasound elements, the delivered drug and ultrasound energy providing the therapeutic effect to the vessel.

2. The catheter of claim 1, further comprising:

a temperature sensor.

3. The catheter of claim 2, wherein the temperature sensor is positioned to detect the temperature of a surface of an ultrasound element.

4. The catheter of claim 2, further comprising:

a feedback control system configured to adjust a level of ultrasound delivered from the plurality of ultrasound elements in response to a signal from the temperature sensor.

5. The catheter of claim 1, further comprising:

a plurality of temperature sensors.

6. The catheter of claim 1, further comprising:

a feedback control system for adjusting a level of ultrasound delivered from a particular ultrasound elements in response to a signal from a particular temperature sensor.

7. The apparatus of claim 1, further comprising:

at least one second drug delivery port coupled with the lumen.

8. The catheter of claim 7, wherein the at least one second drug delivery port is positioned between adjacent ultrasound elements.

9. The catheter of claim 7, further comprising:

a second lumen extending through the catheter; and at least one second drug delivery port coupled with the second lumen to deliver a drug from the second lumen to the vessel.

10. The catheter of claim 1, further comprising:

a flexibility providing structure positioned between a two of the plurality of ultrasound elements.

11. The catheter of claim 10, wherein the flexibility providing structure is at least one rib.

12. The catheter of claim 10, wherein the flexibility providing structure is a braided material.

13. The catheter of claim 10, wherein the flexibility providing structure is a mesh material.

14. The catheter of claim 1, wherein a first portion of each ultrasound element is coupled with a common wire and a second portion of each ultrasound element is coupled with a different wire.

15. The catheter of claim 1, wherein each of the plurality of ultrasound elements are connected in series.

16. The catheter of claim 1, wherein each of the plurality of ultrasound elements are connected in parallel.

17. The catheter of claim 1, wherein each of the plurality of temperature sensors are connected through a common wire.

18. A catheter for providing a therapeutic effect to a vessel of a body, comprising:

an elongated body having a lumen coupled with a drug delivery port through which a drug within the lumen can exit the lumen;

a plurality of ultrasound elements coupled to the elongated body where each of the plurality of ultrasound elements is separated from an adjacent ultrasound element and at least two of the ultrasound elements are positioned on opposite sides of the drug delivery port; and close enough to the drug delivery port that a drug delivered from the drug delivery port is exposed to ultrasound energy delivered from at least one of the ultrasound elements, the delivered drug and ultrasound energy providing the therapeutic effect to the vessel; and a flexibility providing structure positioned between two ultrasound elements among the plurality of ultrasound elements.

19. The catheter of claim 18, wherein the flexibility providing structure is at least one rib.

20. The catheter of claim 18, wherein the flexibility providing structure is a braided material.

21. The catheter of claim 18, wherein the flexibility providing structure is a mesh material.

22. A catheter for providing a therapeutic effect to a vessel of a body, comprising:

an elongated body having a lumen coupled with a plurality of drug delivery ports through which a drug within the lumen can exit the lumen;

a plurality of ultrasound elements coupled to the elongated body where each of the plurality of ultrasound elements is separated from an adjacent ultrasound element and is close enough to one of plurality of drug delivery ports that a drug delivered from the drug delivery port is exposed to ultrasound energy delivered from the ultrasound element, the delivered drug and ultrasound energy providing the therapeutic effect to the vessel.

* * * * *